(12) United States Patent
Diolaiti

(10) Patent No.: US 11,376,088 B2
(45) Date of Patent: Jul. 5, 2022

(54) SYSTEMS AND METHODS FOR HAPTIC FEEDBACK IN SELECTION OF MENU ITEMS IN A TELEOPERATIONAL SYSTEM

(71) Applicant: INTUITIVE SURGICAL OPERATIONS, INC., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 373 days.

(21) Appl. No.: 16/628,958

(22) PCT Filed: Jun. 29, 2018

(86) PCT No.: PCT/US2018/040475
§ 371 (c)(1),
(2) Date: Jan. 6, 2020

(87) PCT Pub. No.: WO2019/010097
PCT Pub. Date: Jan. 10, 2019

(65) Prior Publication Data
US 2020/0222138 A1 Jul. 16, 2020

Related U.S. Application Data

(60) Provisional application No. 62/529,038, filed on Jul. 6, 2017.

(51) Int. Cl.
*A61B 34/00* (2016.01)
*A61B 34/35* (2016.01)

(52) U.S. Cl.
CPC .............. *A61B 34/76* (2016.02); *A61B 34/35* (2016.02); *A61B 34/74* (2016.02)

(58) Field of Classification Search
CPC ......... A61B 34/76; A61B 34/35; A61B 34/74; A61B 34/25; A61B 34/37; G06F 3/014; G06F 3/016
See application file for complete search history.

(56) References Cited

U.S. PATENT DOCUMENTS

6,219,032 B1 * 4/2001 Rosenberg ............ A63F 13/285
345/157
2004/0100440 A1   5/2004 Levin et al.
(Continued)

FOREIGN PATENT DOCUMENTS

EP      2457534 A1    5/2012
WO   WO-2016077543 A1   5/2016
(Continued)

OTHER PUBLICATIONS

International Search Report and Written Opinion for Application No. PCT/US2018/040475, dated Dec. 18, 2018, 18 pages.
(Continued)

*Primary Examiner* — Julian W Woo
(74) *Attorney, Agent, or Firm* — Haynes and Boone, LLP

(57) ABSTRACT

A haptic feedback method comprises providing a teleoperational control system including a first operational mode for operating a teleoperational instrument in response to movement of a control device in a first degree of freedom and a second operational mode for controlling a graphical user interface. The method also includes engaging the second operational mode of the teleoperational control system. While in the second operational mode, the method includes tracking movement of the control device of in a second degree of freedom, different from the first degree of freedom. While in the second operational mode and responsive to the movement of the control device in the second degree of freedom, the method includes applying, by a teleopera-
(Continued)

tional control system, a first haptic force to the control device.

20 Claims, 10 Drawing Sheets

(56) References Cited

U.S. PATENT DOCUMENTS

| | | |
|---|---|---|
| 2011/0118752 A1 | 5/2011 | Itkowitz |
| 2011/0218774 A1* | 9/2011 | Ikits .................... G06F 3/016 703/1 |
| 2013/0169423 A1 | 7/2013 | Iorgulescu |
| 2013/0211590 A1 | 8/2013 | Diolaiti et al. |
| 2014/0005682 A1 | 1/2014 | Worrell et al. |
| 2015/0150639 A1 | 6/2015 | Diolaiti et al. |
| 2016/0228204 A1* | 8/2016 | Quaid .................. A61B 34/71 |

FOREIGN PATENT DOCUMENTS

| | | |
|---|---|---|
| WO | WO-2016077552 A1 | 5/2016 |
| WO | WO-2018013197 A1 | 1/2018 |

OTHER PUBLICATIONS

Vertut, Jean and Phillips Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2018/040475 dated Jan. 16, 2020, 8 pages.
Extended European Search Report for Application No. EP18828360 dated Mar. 3, 2021, 9 pages.

* cited by examiner

SYSTEMS AND METHODS FOR HAPTIC FEEDBACK IN SELECTION OF MENU ITEMS IN A TELEOPERATIONAL SYSTEM

CROSS-REFERENCE TO RELATED APPLICATIONS

This patent application is the U.S. national phase of International Application No. PCT/US2018/040475, filed Jun. 29, 2018, which designated the U.S. and claims priority to and the benefit of the filing date U.S. Provisional Application 62/529,038, filed Jul. 6, 2017, all of which are incorporated by reference herein in their entirety.

FIELD

The present disclosure is directed to systems and methods for controlling operation of a teleoperational control system and more particularly to systems and methods for providing haptic feedback to a user when accessing a graphical user interface menu using control devices of the teleoperational control system.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Some minimally invasive medical instruments may be teleoperated or otherwise computer-assisted. A variety of control devices may be used to control teleoperated or computer-assisted medical tools. To extend the functionality of teleoperated systems without adding additional structural controls to the user's control console, graphical user interfaces may be used. Systems and methods are provide haptic feedback to the user when accessing graphical user interfaces using control devices that are also used to control instruments in the patient anatomy.

SUMMARY

The embodiments of the invention are summarized by the claims that follow below.

In one embodiment a haptic feedback method comprises providing a teleoperational control system including a first operational mode for operating a teleoperational instrument in response to movement of a control device in a first degree of freedom and a second operational mode for controlling a graphical user interface. The method also includes engaging the second operational mode of the teleoperational control system. While in the second operational mode, the method includes tracking movement of the control device of in a second degree of freedom, different from the first degree of freedom. While in the second operational mode and responsive to the movement of the control device in the second degree of freedom, the method includes applying, by a teleoperational control system, a first haptic force to the control device.

In another embodiment, a haptic feedback method comprises engaging an interface mode of a teleoperational control system. Responsive to movement of a control device of the teleoperational control system, the method further comprises, from a nominal position, applying a first haptic force to the control device urging the control device toward the nominal position. The method also includes determining that the control device has moved, from a nominal position, a first displacement distance in a first degree of freedom to an engaged position. The method also includes applying a second haptic force to the control device to provide a haptic sensation indicative of an engaged operational state. The method also includes applying a third haptic force to the control device to urge a return of the control device from the engaged position toward the nominal position while in the engaged operational state.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 9 is a flowchart illustrating another method of providing haptic feedback through a control device of a teleoperational system when using a graphical user interface menu.

DETAILED DESCRIPTION

Figure 1A:
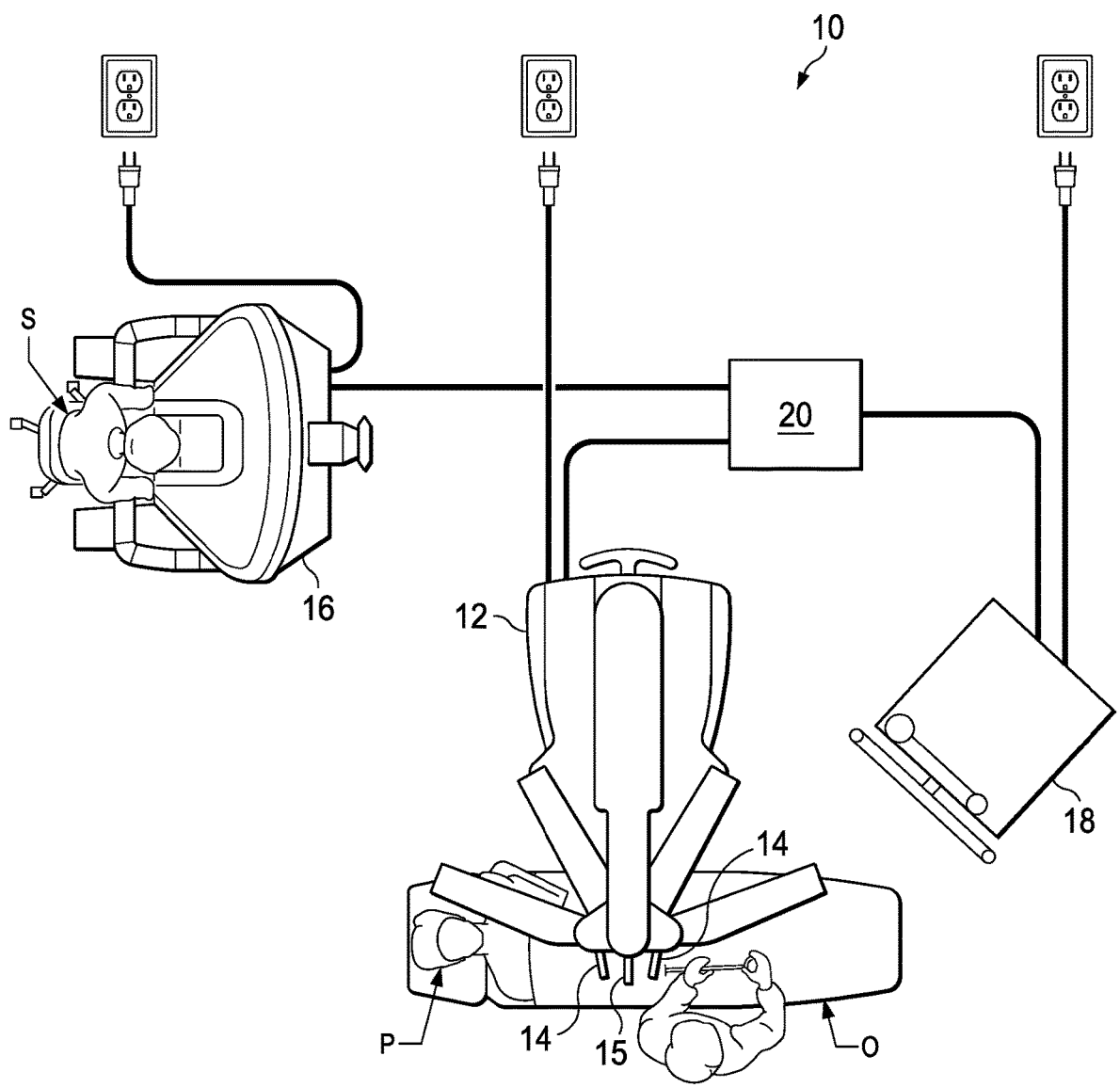
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom e.g., roll, pitch, and yaw).

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z axes of a Cartesian reference frame) and in three degrees of rotational motion (e.g., rotation about the Y, Z Cartesian axes). Additionally, the motors can be used to actuate an articulable end effector of the instrument for grasping tissue in the jaws of a biopsy device or the like. Electric motors can be controlled to generate a commanded torque (or force, in the case of a linear motor).

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
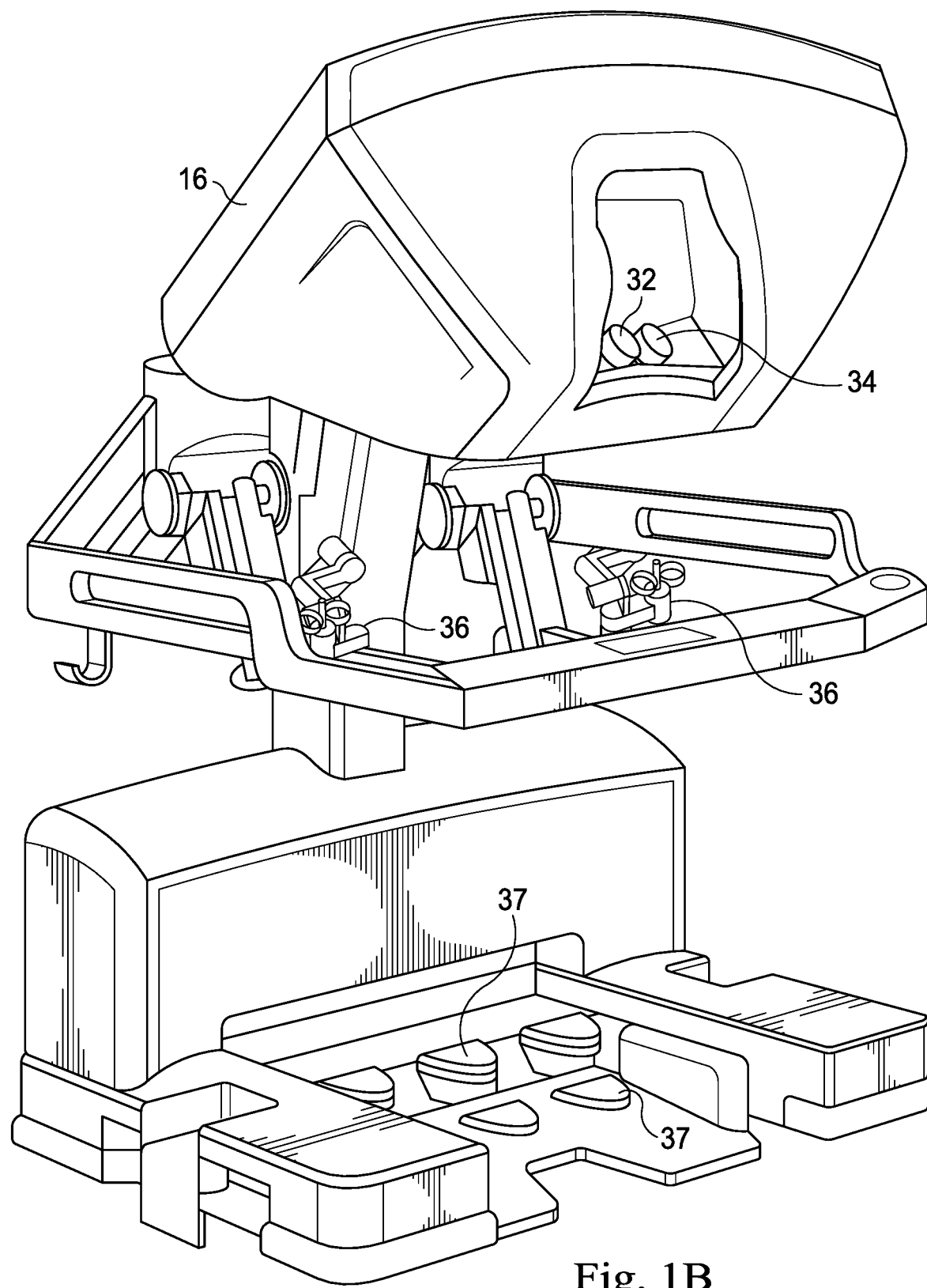
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, 37 which are used by the surgeon to execute functions of the system 10. The input control devices 36 are hand operated input control devices which cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. The input control devices 37 allow the system 10 to shift between operational modes. The devices 37 may be pedals operated by the surgeon's foot or may be other types of hand or foot switches that serve as a clutch device to disengage a first operational mode and engage a second operational control mode. Operational modes of the teleoperational medical system 10 may include, for example, a surgical instrument control mode, a camera control mode, a menu control mode, and the like. A surgical instrument control mode may allow the surgeon to control manipulation of the instruments 14 as described above. A camera control mode may allow the surgeon to use the input control devices 36 to cause the teleoperational assembly 12 to manipulate the endoscopic imaging system 15. A menu control mode may allow the surgeon to use input control devices 36 to navigate a graphical user interface menu displayed to the surgeon via left and right eye displays 32 and 34. The control device 37 may be depressed, for example, to transition between the surgical instrument control mode and the menu mode.

Figure 1C:
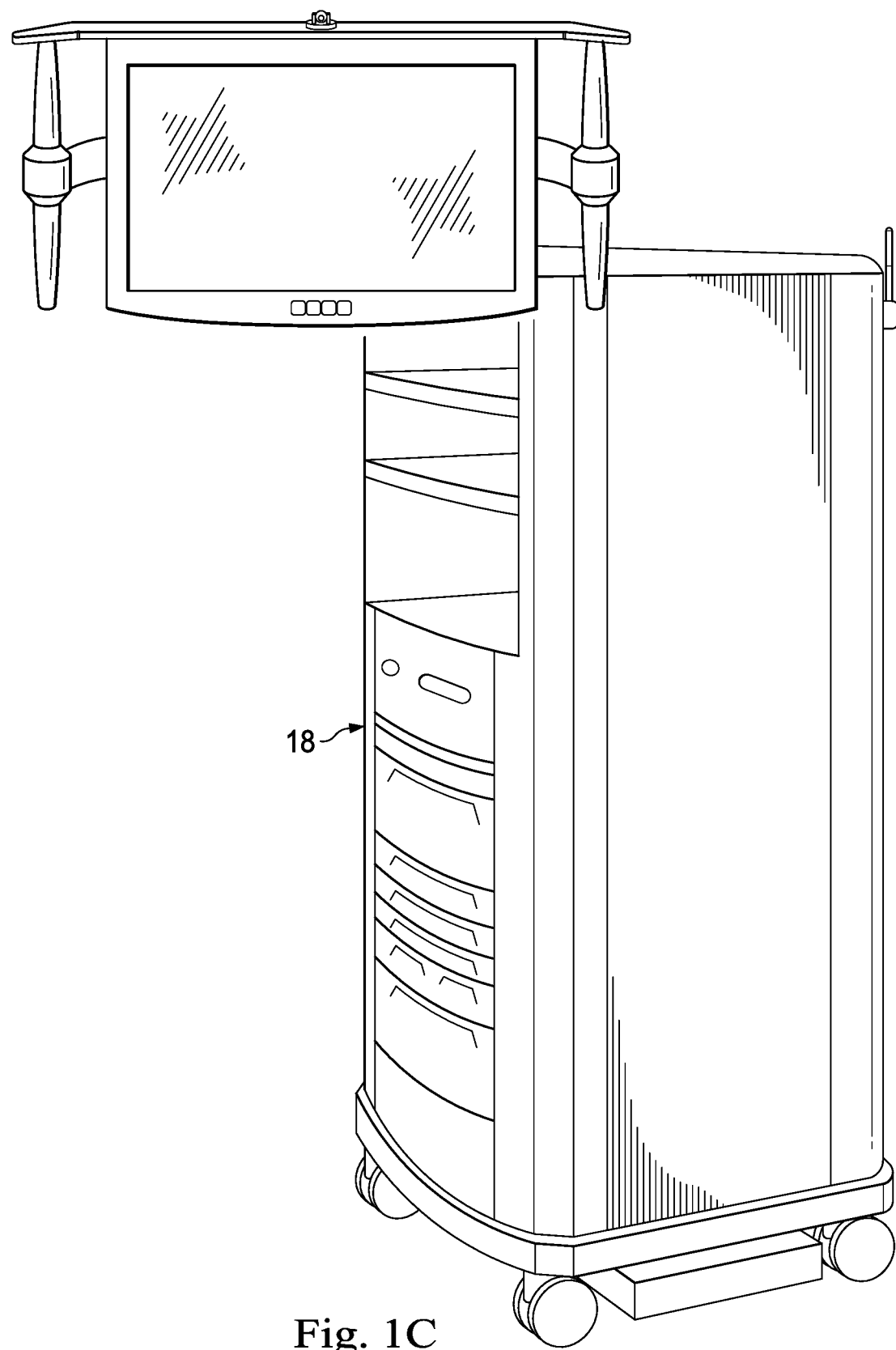
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
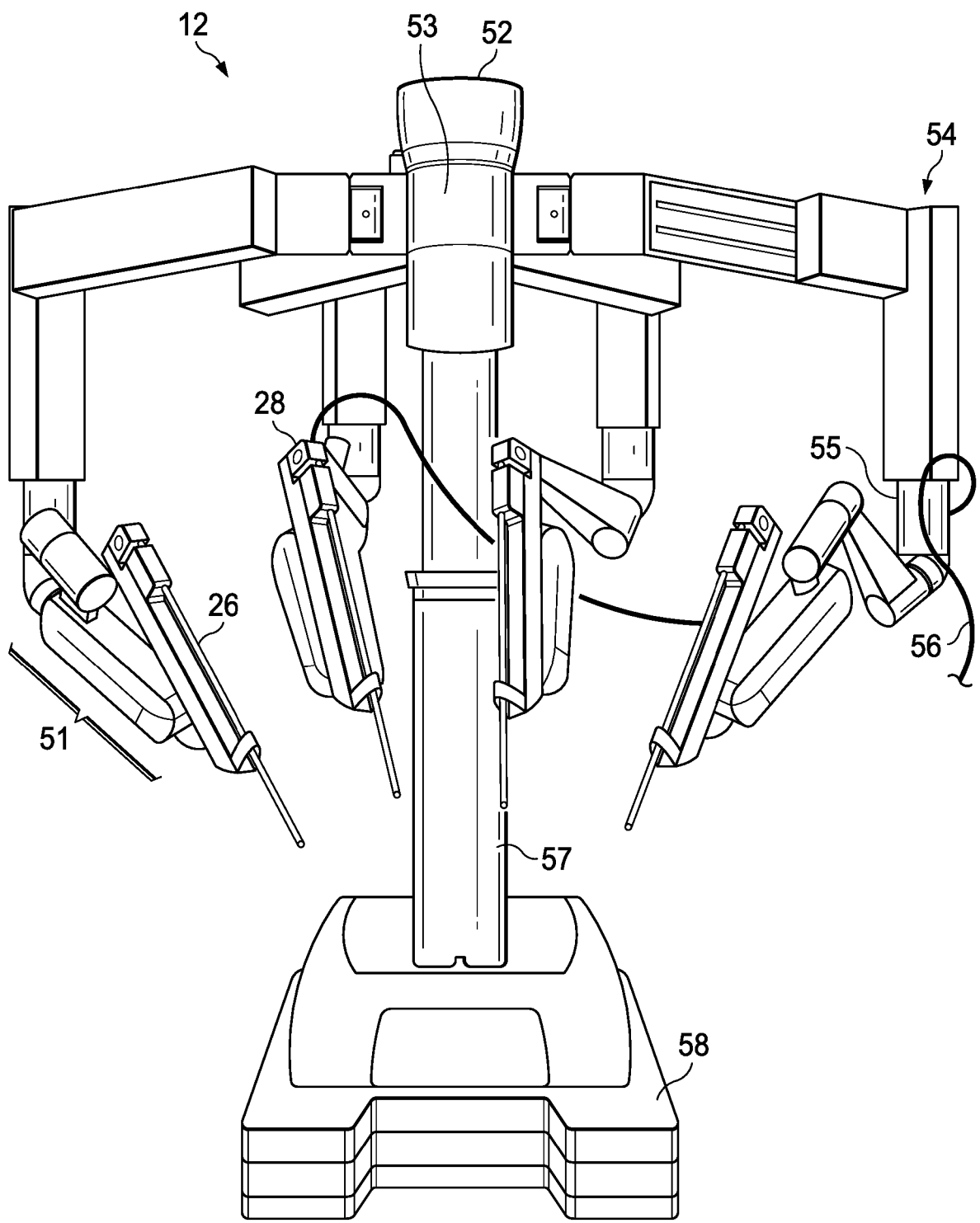
FIG. 1D is a perspective view of a patient side cart, according to one example of principles described herein.

FIG. 1D is a perspective view of one embodiment of a teleoperational assembly 12 which may be referred to as a patient side cart. The patient side cart 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Endoscopes may be provided with different viewing angles including a 0° viewing angle for forward axial viewing or viewing angles between 0°-90° for forward oblique viewing. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy.

In order to extend the functionality of the teleoperational medical system 10 without adding additional structural appendages, such as foot pedals, physical switches, dials, and buttons to the control console 16, graphical user interface menus may be used to provide additional options and actions for operating the system 10. When using graphical user interface menus to offer additional functions of the system 10, it is helpful to provide haptic feedback to the operator at the control console 16 to facilitate interaction with the elements of the graphical user interface menu and to provide confirmation that commands have been executed. Other feedback mechanisms such as auditory and visual feedback cues may also provide confirmation that commands have been executed. The use of haptic feedback when using graphical interface menus may provide a sense of immersion for the user.

Figure 2:
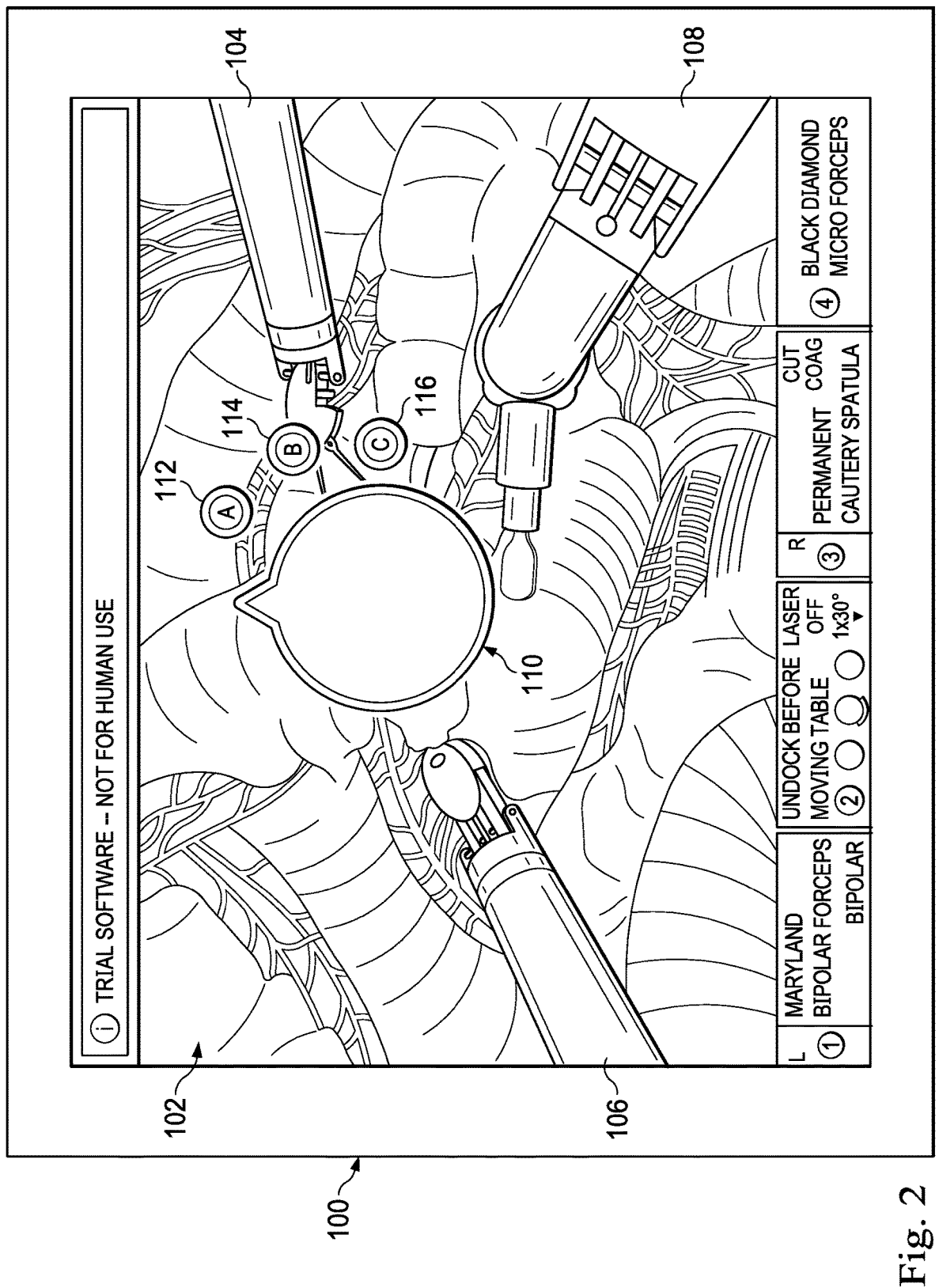
FIG. 2 illustrates a graphical user interface including a selector icon.
Figure 3A:
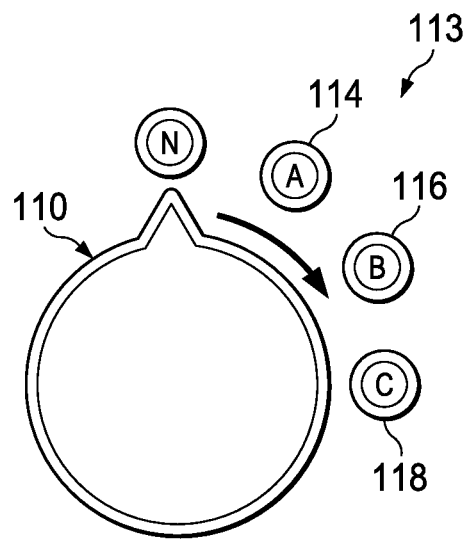
FIG. 3A illustrates the selector icon of FIG. 2 in a nominal position.

FIG. 2 illustrates a display 100 visible through the left eye display 32 and the right eye display 34 of the surgeon's console 16. In this embodiment, the display include a view of the surgical environment 102 including medical tools 104, 106, 108. In surgical instrument control or "following" operational mode of the teleoperational system, the control devices 36 may be manipulated to control movement of the tools 104, 106, 108 in limited or unlimited degrees of freedom. For example, in the surgical instrument control mode, the control devices may be operable to move the instruments only in three degrees of translational freedom in Cartesian coordinate space. When a graphical user interface mode of the teleoperational system is invoked (e.g., by depressing a clutch pedal 37), the control devices 36 become decoupled from the tools 104, 106, 108 and can instead be used to select items from a graphical user interface menu. FIG. 2 illustrates a graphical user interface menu including a selector icon 110 and a plurality of menu items 112, 114, 116. The graphical user interface menu 113 may be superimposed on the image of the surgical environment 102 as shown in FIG. 2 or alternatively, only the graphical user interface menu may be displayed, without the surgical environment. In the graphical user interface mode with the tools 104, 106, 108 uncoupled from the control devices 36, one or more of the control devices may be coupled to move the selector icon 110 between a nominal or neutral position (as shown in FIG. 2) and the menu items 112, 114, 116. In one embodiment, menu item 112 may be associated with an endoscopic camera control mode in which the camera may be repositioned, FIG. 3A illustrates the selector icon 110 of FIG. 2 in a nominal position and having a clockwise direction of movement that corresponds to clockwise movement of a control device 36 about the rotational axis of the control device. The nominal position of the control device 36 may be located in space wherever the control device was positioned and oriented when the graphical user interface mode was engaged. Thus, the location of the nominal position of the control device 36 in space may be different each time the interface mode is engaged.

Movement of the selector icon 110 may be coupled to the right or left hand control device. Different graphical user interface menus maybe associated with each hand so that the right hand selects from a first menu and the left hand selects from a second menu. The menu may, alternatively, be configured so that the menu items are selected by counter-clockwise rotation. The rotational movement of the control device 36 used to move the selector icon 110 may be a degree of freedom that is not used to operate the tools when the system in other modes of operation such as the surgical instrument control mode. Thus, the user recognizes that the roll degree of freedom about the axis of the control device is used for menu selection and not tool operation. In other embodiments, the same degrees of freedom used to control the selector icon may be used to control tool movement in the surgical instrument control mode. In other embodiments, the control device may move in both clockwise and counterclockwise directions to select menu items. For example, clockwise rotation may direct the selector icon toward a menu item for "Active Camera Control Action" and a counter-clockwise rotation may direct the selector icon toward a menu item for an "Active Relocate" action. In other embodiments, the control device may move about other rotational axes or may translate along axes to generate the selection motion. In other words, any Cartesian translational or rotational motion may generate the selection motion.

Figure 5:
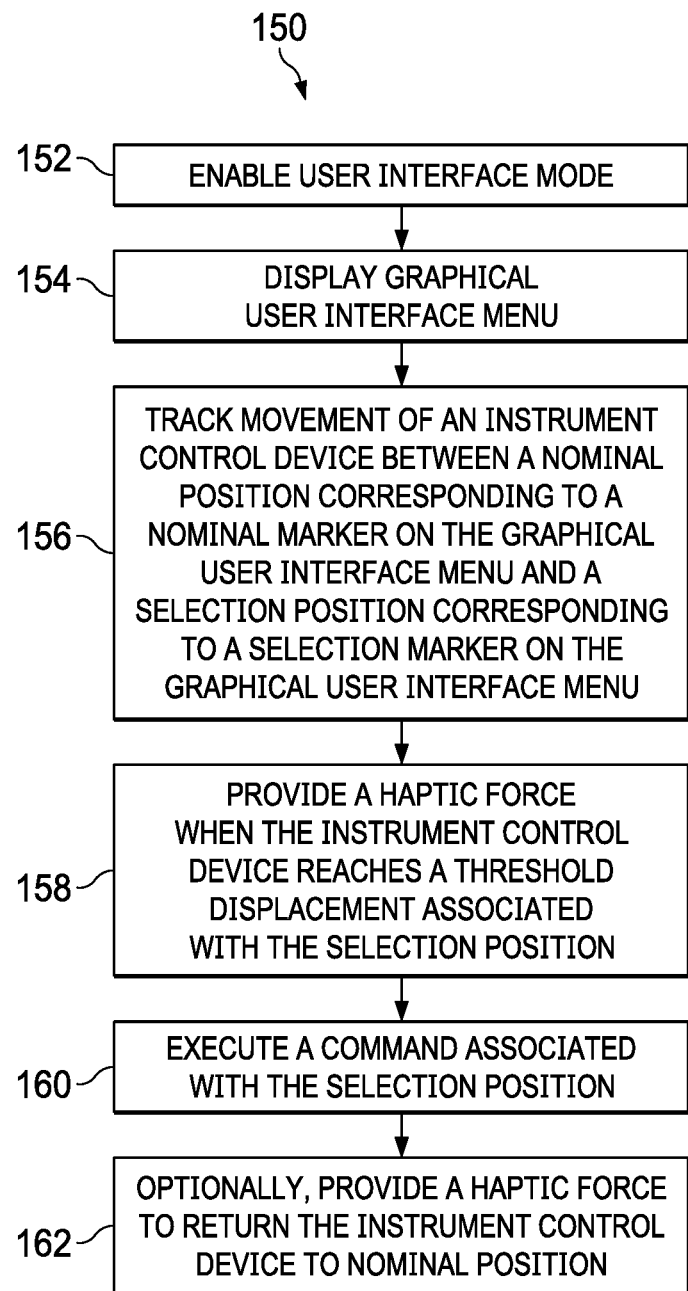
FIG. 5 is a flowchart illustrating a method of providing haptic feedback through a control device of a teleoperational system when using a graphical user interface menu.

Referring now to FIG. 5, a flowchart 150 illustrates a method of providing haptic feedback through a control device of a teleoperational system, such as system 10, when using a graphical user interface menu, such as the menu 113. Prior to initiating the process shown in flowchart 150, the system 10 may be in a surgical instrument control mode or another operational mode of the system. At a process 152, the control system 20 determines whether an input control device 37 has been actuated to initiate a graphical user interface mode of the system 10. This mode may be enabled, for example, by depressing a clutch pedal 37 of the surgeon's console to disengage from the surgical instrument control mode, including decoupling the surgical instruments from the control devices 36, and engaging the graphical user interface control mode, including coupling at least one of the control devices to a graphical user interface menu selector icon. At a process 154, the menu 113 is displayed either with or without the image of the surgical environment. If, for example, the menu 113 is associated with an instrument visible in the surgical environment, the menu may appear near a distal tip of that instrument.

Figure 3B:
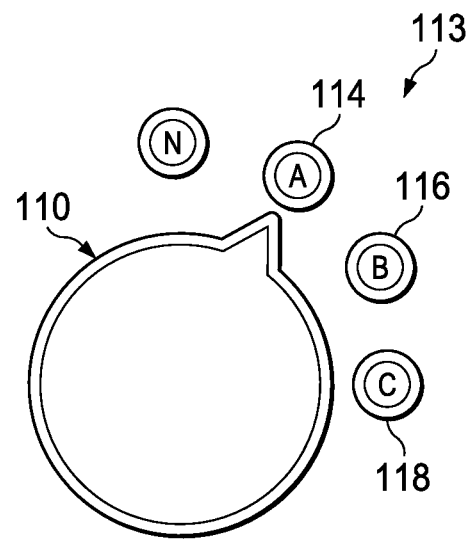
FIG. 3B illustrates the selector icon of FIG. 2 rotated to an engaged position.

At a process 156, the system 10 receiving and tracking control signals from the control device 36 indicating that the control device is being moved in a clockwise direction about the axis of the shaft of the control device. Accordingly, the selector icon 110 moves counterclockwise from a nominal position N (see FIG. 3A) toward menu item A as shown in FIG. 3B.

At a process 158, a haptic force such as a haptic torque is provided to the control device when the instrument control device is moved a threshold displacement distance associated with a selection position corresponding to the menu item A 114. The haptic torque may be superimposed on the normal torque produced by the controller. The haptic torque provides a haptic detent or sensation to the user indicating that the controller has selected the menu item A. The normal torque may be, for example, a torque generated to reflect to the user a tracking error that the teleoperational assembly has with respect to the control device position/orientation.

At a process 160, a command associated with the menu item A is executed in response to a user input (e.g., pressing a physical button on the control device). For example the menu item A may initiate camera control. Alternatively, and particularly if there is a single menu item, the execution of the command may occur when the control device reaches the selected position. Optionally, the selector icon 110 and the control device 36 may remain in the selected position, awaiting further movement of the control device to move the selector icon clockwise to menu item B 116 or counter-clockwise to the nominal position.

Figure 3C:
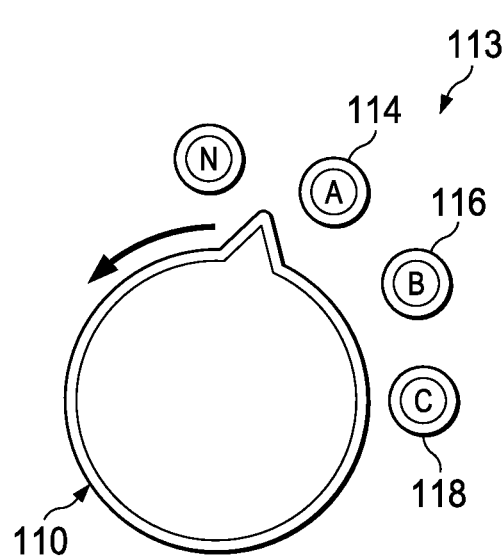
FIG. 3C illustrates the selector icon of FIG. 2 returning to the nominal position from the engaged position.

At a process 162, optionally, another haptic torque may be provided to move the control device 36 and the selector icon 110 back to the nominal position after the command for menu item A is executed at process 160 (see FIG. 3C). With this technique of re-centering the selector icon and control device 36 to a nominal position, a counter module may be used to count each time the selector icon and control device 36 return to the nominal position from the selection position. In this embodiment, a counter value of the counter module is incremented each time the selector icon and control device 36 return to the nominal position from the selection position. Each count increment of the counter module may be associated with a menu item, allowing the user to toggle through a items in a menu with repeated reciprocal movements of the control device 36. For example, one click (e.g., one count of movement to the selection position and a return to the nominal position) may correspond to a first menu item and two clicks may correspond to a second menu item. The incremented menu items may be displayed to the user. Using the counter module requires the user to rotate the control device only a limited distance (e.g. to menu item A) to toggle through several menu items rather than requiring the user to rotate the control device far away from the nominal position. This prevents the user from contorting his hand to reach large angle positions and allows the user's hand to always be close to the nominal position where he can quickly change modes and resume control of the surgical instruments coupled to the control devices 36.

Figure 4:
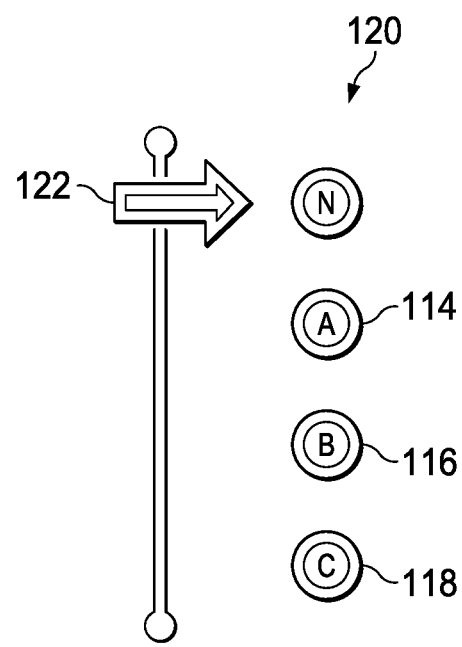
FIG. 4 illustrates a selector icon according to an alternative embodiment.

FIG. 4 illustrates an alternative graphical user interface menu 120 in which a selector icon 122 moves in a translational direction. Other menu arrangements in which the control device and the selector icon move in other single degrees of freedom may be used.

In an alternative embodiment, either a clockwise motion of the control device 36 or a counter-clockwise motion of the control device may result in movement of the selector icon 110 in a clock-wise direction or may result in movement of the selector icon 122 in a single translational direction. In other words, a motion of the control device 36 in either the right or the left roll direction would result in the same single advancement of the selector icon. A haptic detent feature or "click" may be felt by the user for each single movement. This embodiment may be suitable for making the movement action easily accessible in multiple postures of the control device 36. For example, when the control device 36 is pointing to the right, it may be easier for the user to twist the roll axis of the control device to the left rather than the right to advance the selector icon. By making the movement action symmetric (i.e., such that either control device can cause the selector advancement), the user has more options for controlling the selector. This feature may be simultaneously active on both right and left control devices. The software may detect which control device crosses the $\delta_1$ threshold to determine which control device is activating the haptic detent feature.

Figure 6:
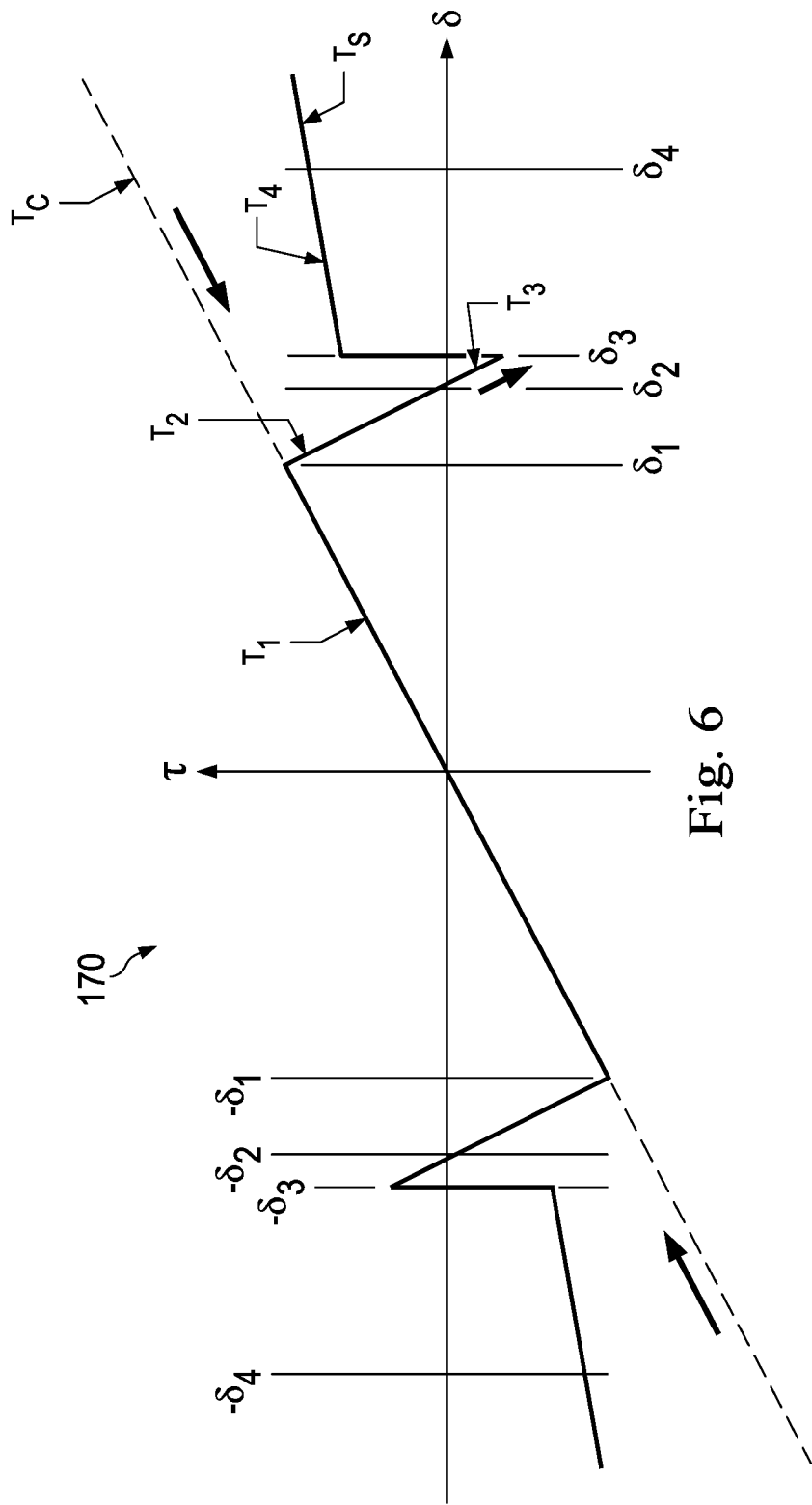
FIG. 6 is a torque profile used to provide haptic feedback according to one embodiment of the disclosure.
Figure 7:
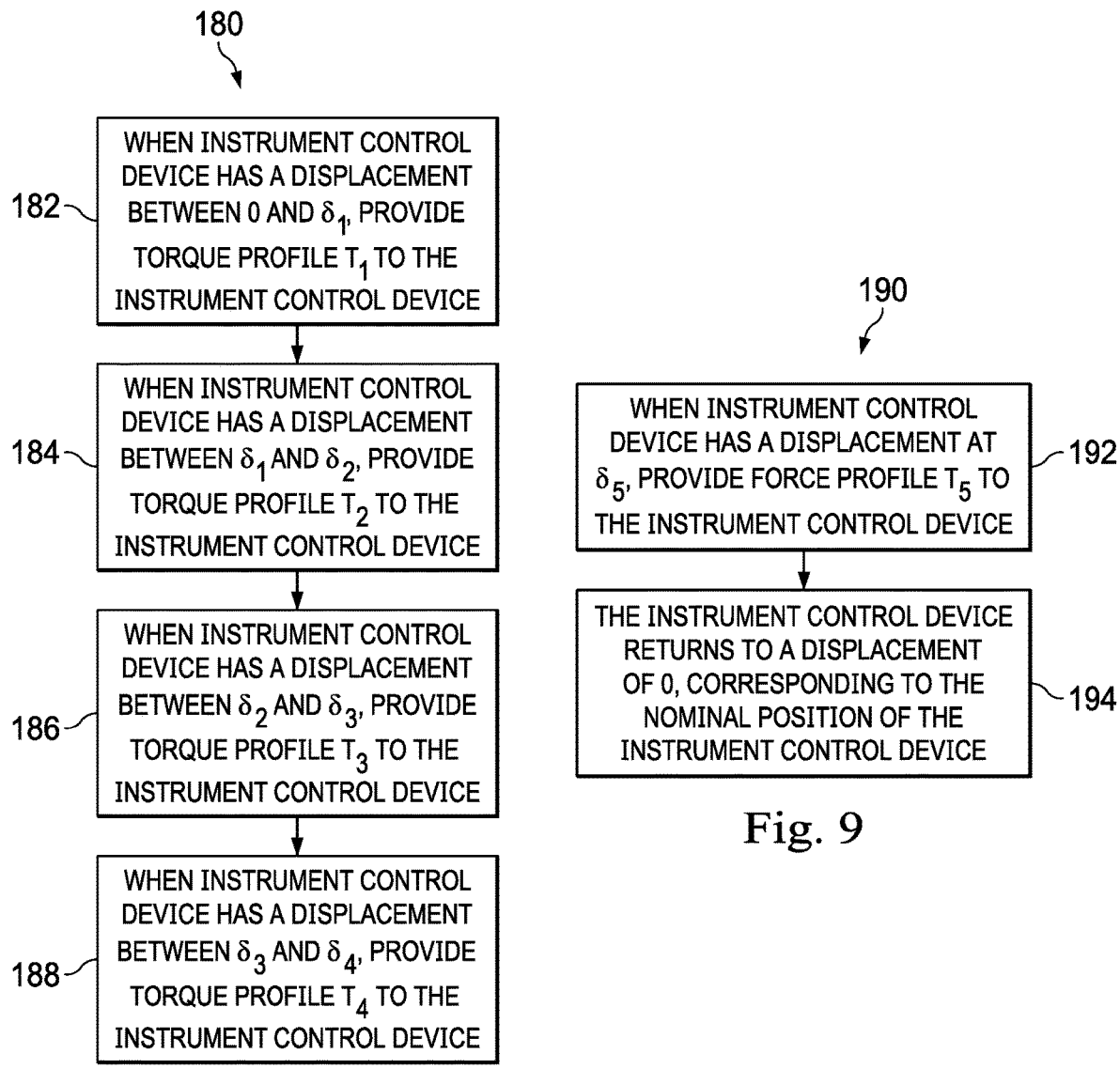
FIG. 7 is a flowchart illustrating another method of providing haptic feedback through a control device of a teleoperational system when using a graphical user interface menu.

FIG. 6 illustrates a haptic detent torque profile $T_S$ superimposed on a controller torque profile $T_C$ used to provide haptic feedback to the control device 36 according to an embodiment in which applied motor torque mimics a rotational spring-loaded button. In this embodiment, the haptic detent torque profile $T_S$ creates the haptic sensation of a spring-loaded button. FIG. 7 is a flow chart 180 describing the torque profile of FIG. 6, The torque profiles are provided to one or more drive actuators in the control device 36 to provide a force feedback felt by the hands of the surgeon S. The controller torque profile $T_C$ provides a centering or force that urges the control device toward the nominal position. Greater torque is applied as the displacement d (e.g., angle of rotation or distance of rotation of the control device 36) increases, and the hand of the surgeon on the control device feels increasing resistance of the control device as the displacement increases. The nominal position is located where a displacement $\delta$ equals zero. The haptic detent torque profile $T_S$ superimposed on the controller torque profile $T_C$ has several zones.

With reference to 6 and 7, at a process 182, when the control device has a displacement (from nominal) within a displacement zone between zero and $\delta_1$, a torque profile $T_1$ follows the controller torque profile $T_C$, providing no additional resistance torque beyond the torque profile $T_C$. At a process 184 when the control device has a displacement in a displacement zone between $\delta_1$ and $\delta_2$, a torque profile $T_2$ has a steep negative slope away from the torque profile $T_C$. That is, the resistive force experienced by the surgeon decreases suddenly. At a process 186 when the control device has a displacement in a displacement zone between $\delta_2$ and $\delta_3$, a torque profile $T_3$ has a torque sign inversion that provides a force that urges the control device away from the nominal position and toward a displacement distance $\delta_2$. The torque profile $T_3$ provides the haptic sensation of a sharp push toward the button "click" or engaged point that occurs at the displacement distance $\delta_3$. At a process 188 once the control device has reached a displacement distance $\delta_3$, a torque profile $T_4$ provides a centering (toward nominal) force that is smaller than the torque profile $T_C$ at the same displacement distance. As shown in FIG. 6, the torque profiles $T_C$ and $T_S$ have symmetric profiles representing two "button" torque profiles. The symmetric torque profile may provide the same haptic detent sensation but may, occur when the rotational motion of the control device is in the opposite direction. In alternative embodiments, the calculated torque profiles may change at different displacements associated with locations of different menu items and the magnitude of the torque provided may be increased or lessened depending a variety of factors including user preference, the user grip action associated with the detent magnitude, or the time expected between successive actions.

Figure 8:
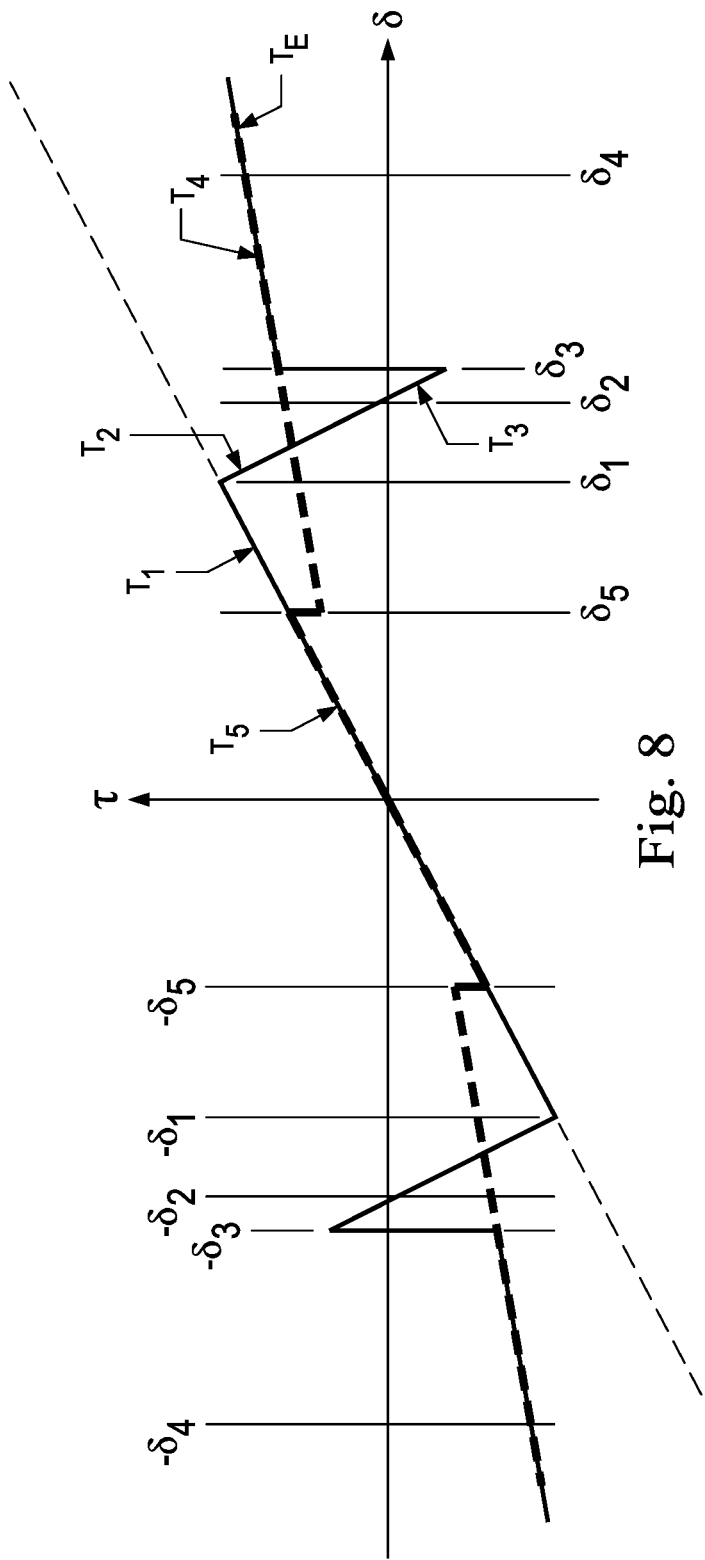
FIG. 8 is a torque profile used to provide haptic feedback according to another embodiment of the disclosure.

FIG. 8 illustrates a haptic detent torque profile $T_E$ superimposed on a controller torque profile $T_C$ used to provide haptic feedback to the control device 36 after the engaged or "clicked" displacement distance $\delta_3$ is reached. In this embodiment, the haptic detent torque profile $T_E$ creates the haptic sensation of an engaged or "clicked" spring-loaded button and a haptic sensation of a recentering detent. FIG. 9 is a flow chart 190 describing the torque profile of FIG. 8. Once the control device 36 has reached a displacement distance $\delta_3$, the torque profile $T_4$ provides a centering (toward nominal) force that is smaller than the torque profile $T_C$ at the same displacement distance. The torque profile $T_4$ is followed until the control device reaches a displacement distance $\delta_5$ on the return to the nominal position. At a process 192, when the control device reaches a displacement distance $\delta_5$, a torque profile $T_5$ provides an increased torque to the level of the controller torque profile $T_C$. When the torque profile T5 is applied to the control device, the user feels a sudden increased resistance over T4. The sudden increase in resistance may cause the user to instinctively relax or release his grip, allowing the control device to re-center to the nominal position where displacement $\delta$ equals zero at a process 194.

In one alternative embodiment, the torque superimposed on the normal control device torque mimics a translational switch that provide ON and OFF switch positions at displacement distances along a line in space. In another alternative embodiment, the torque superimposed on the normal control device torque mimics a rotational switch that provides ON and OFF switch positions at angular displacement distances about an axis in space. This embodiment may be similar to the button embodiment described in detail above except without providing a re-centering force to move the control device toward the nominal position. Instead, the control device remains in the selected position (i.e. "clicked state") until the action is executed, at which point the detent is deactivated or reset. In another alternative embodiment, the torque superimposed on the normal control device torque mimics a spring-loaded translational button with movement along a line in space.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A haptic feedback method comprising:
   providing a teleoperational control system including a first operational mode for operating a teleoperational instrument in response to movement of a control device in a first degree of freedom and a second operational mode for controlling a graphical user interface;
   engaging the second operational mode of the teleoperational control system;
   while in the second operational mode, tracking movement of the control device in a second degree of freedom, different from the first degree of freedom; and
   while in the second operational mode and responsive to the movement of the control device in the second degree of freedom, applying, by the teleoperational control system, a first haptic force to the control device.

2. The haptic feedback method of claim 1 further comprising:
   determining that the control device has moved, from a nominal position, a first displacement distance in the second degree of freedom to an engaged position; and
   applying a second haptic force to the control device to provide a haptic sensation indicative of an engaged state of the second operational mode.

3. The haptic feedback method of claim 2 wherein the second haptic force provides a haptic sensation indicative of an initial stage of the engaged state, the method further comprising:
   applying a third haptic force, inverted from the second haptic force, to the control device to urge the control device to the engaged position, the third haptic force providing a haptic sensation indicative of a full stage of the engaged state of the second operational mode.

4. The haptic feedback method of claim 2 further comprising:
   applying a third haptic force to the control device to urge the control device toward the nominal position.

5. The haptic feedback method of claim 4 further comprising:
   incrementing a counter value when the control device returns to the nominal position.

6. The haptic feedback method of claim 4 further comprising:
   determining that the control device is at a third displacement distance from the nominal position; and
   applying a fourth haptic force, greater than the third haptic force, to the control device to urge the control device toward the nominal position.

7. The haptic feedback method of claim 4 wherein the third haptic force is less than the first haptic force.

8. The haptic feedback method of claim 2 wherein the graphical user interface includes a selector icon, a nominal marker, and a selection marker and wherein the selector icon identifies the nominal marker when the control device is in the nominal position and identifies the selection marker when the control device is in the engaged position.

9. The haptic feedback method of claim 1 wherein the second degree of freedom is a rotational degree of freedom about a rotational axis of the control device.

10. The haptic feedback method of claim 9 wherein the first degree of freedom is a linear degree of freedom.

11. The haptic feedback method of claim 1 wherein the teleoperational instrument is an endoscopic camera.

12. The haptic feedback method of claim 1 wherein the teleoperational instrument includes an end effector.

13. A haptic feedback method comprising:
engaging an interface mode of a teleoperational control system;
responsive to movement of a control device of the teleoperational control system, from a nominal position, applying a first haptic force to the control device urging the control device toward the nominal position;
determining that the control device has moved, from the nominal position, a first displacement distance in a first degree of freedom to an engaged position;
applying a second haptic force to the control device to provide a haptic sensation indicative of an engaged operational state; and
applying a third haptic force to the control device to urge a return of the control device from the engaged position toward the nominal position while in the engaged operational state.

14. The haptic feedback method of claim 13 wherein the second haptic force provides a haptic sensation indicative of an initial stage of the engaged operational state, the method further comprising:
applying a fourth haptic force, inverted from the second haptic force, to the control device to urge the control device to the engaged position, the fourth haptic force providing a haptic sensation indicative of a full stage of the engaged operational state.

15. The haptic feedback method of claim 13 further comprising:
incrementing a counter value when the control device returns to the nominal position.

16. The haptic feedback method of claim 13 further comprising:
determining that the control device is at a third displacement distance from the nominal position; and
applying a fourth haptic force, greater than the third haptic force, to the control device to urge the control device toward the nominal position.

17. The haptic feedback method of claim 13 wherein movement of the control device in the first degree of freedom is in a rotational degree of freedom about a rotational axis of the control device.

18. The haptic feedback method of claim 13 further comprising:
displaying a graphical user interface that includes a selector icon, a nominal marker, and a selection marker and wherein the selector icon identifies the nominal marker when the control device is in the nominal position and identifies the selection marker when the control device is in the engaged position.

19. The haptic feedback method of claim 13 wherein the teleoperational control system includes an instrument control mode for operating a teleoperational instrument in response to movement of the control device in a second degree of freedom, different from the first degree of freedom.

20. The haptic feedback method of claim 13 wherein the teleoperational control system includes an instrument control mode for operating a teleoperational instrument in response to movement of the control device in a plurality of degrees of freedom, wherein the plurality of degrees of freedom does not include the first degree of freedom.

* * * * *